United States Patent
Zanatta et al.

(10) Patent No.: US 10,617,424 B2
(45) Date of Patent: Apr. 14, 2020

(54) METHOD FOR TESTING INSURGENCE OF SPINAL ISCHEMIA DUE TO ENDOVASCULAR TREATMENT OF AORTIC ANEURISMS

(71) Applicants: Paolo Zanatta, Mogliano Veneto (IT); Fabrizio Farneti, Treviso (IT)

(72) Inventors: Paolo Zanatta, Mogliano Veneto (IT); Fabrizio Farneti, Treviso (IT)

(73) Assignee: BE SAFE Srl, Legnaro (VR) (IT)

( * ) Notice: Subject to any disclaimer, the term of this patent is extended or adjusted under 35 U.S.C. 154(b) by 162 days.

(21) Appl. No.: 15/656,984

(22) Filed: Jul. 21, 2017

(65) Prior Publication Data
US 2017/0319215 A1 Nov. 9, 2017

Related U.S. Application Data

(63) Continuation of application No. 14/116,021, filed as application No. PCT/IB2012/052302 on May 9, 2012, now abandoned.

(30) Foreign Application Priority Data

May 10, 2011 (IT) ............... MI2011A0796

(51) Int. Cl.
*A61B 17/12* (2006.01)
*A61F 2/07* (2013.01)
(Continued)

(52) U.S. Cl.
CPC .......... *A61B 17/12113* (2013.01); *A61F 2/07* (2013.01); *A61F 2/90* (2013.01); *A61F 2002/075* (2013.01); *A61F 2002/9528* (2013.01)

(58) Field of Classification Search
CPC .............. A61F 2/07; A61F 2002/072; A61F 2002/075; A61F 2002/077; A61B 17/12109; A61B 17/12113
See application file for complete search history.

(56) References Cited

U.S. PATENT DOCUMENTS 6,221,096 B1 * 4/2001 Alba ................. A61F 2/86
606/108
8,926,680 B2 * 1/2015 Ferrara ............ A61B 17/12022
623/1.11

(Continued)

FOREIGN PATENT DOCUMENTS

| WO | WO2008016578 A1 | 2/2008 |
| WO | WO2010026240 A1 | 3/2010 |
| WO | WO2011006013 A1 | 1/2011 |

OTHER PUBLICATIONS

Ishimaru, et al. "Preliminary report on prediction of spinal cord ischemia in endovascular stent graft repair of thoracic aortic aneurysm by retrievable stent graft" J Thor and Cardiovasc Surg Apr. 1998; 811-18 (Year: 1998).*

(Continued)

*Primary Examiner* — Thomas M McEvoy
(74) *Attorney, Agent, or Firm* — Robert J. Ballarini

(57) ABSTRACT

A removable implantable medical device (1) for the endovascular treatment of aneurysm, particularly of aneurysm of the thoracic aorta, comprising a supporting structure (2) tubular in shape and covered externally by a covering (3). The supporting structure (2) and the covering (3) define a duct (4) for blood circulation.
The device is provided with extraction means (5) for extracting the duct (4) from the body of the subject in whom it is inserted. The extraction means (5) are associated with the duct (4) and communicate with the outside of the body.

11 Claims, 3 Drawing Sheets

(51) Int. Cl.
*A61F 2/95* (2013.01)
*A61F 2/90* (2013.01)

(56) References Cited

U.S. PATENT DOCUMENTS

| | | |
|---|---|---|
| 2005/0131515 A1 | 6/2005 | Cully |
| 2006/0041271 A1 | 2/2006 | Bosma et al. |
| 2009/0017441 A1 | 1/2009 | Peng et al. |
| 2009/0171441 A1 | 7/2009 | Osborne |
| 2013/0297003 A1 | 11/2013 | Pinchuk |
| 2014/0081317 A1 | 3/2014 | Zanatta et al. |

OTHER PUBLICATIONS

Spanos, et al. "Risk of spinal cord ischemia after fenestrated or branched endovascular repair of complex aortic aneurysms" J Vasc Surg. Feb. 2019; 69(2)357-366.

Tiesenhausen, et al. "Cerebrospinal fluid drainage to reverse paraplegia after endovascular thoracic aortic aneurysm repair" J Endovasc Ther. Apr. 2000;7(2):132-5.

Weigang, et al. "Thoracoabdominal aortic aneurysm repair: interplay of spinal cord protecting modalities" Eur J Vasc Endovasc Surg. Dec. 2005;30(6):624-31. Epub Jul. 14, 2005.

Rodriguez, et al. "Application of endograft to treat thoracic aortic pathologies: a single center experience" J Vasc Surg. Sep. 2007;46(3):413-20.

Stone, et al. "Stent-graft versus open-surgical repair of the thoracic aorta: mid-term results" J Vasc Surg. Dec. 2006;44(6):1188-97.

Eagleton, et al. "Spinal and visceral ischemia after endovascular aortic repair" J Cardiovasc Surg (Torino). Feb. 2010;51(1):71-83.

Ishimaru, et al. "Preliminary report on prediction of spinal cord ischemia in endovascular stent graft repair of thoracic aortic aneurysm by retrievable stent graft" J Thor and Cardiovasc Surg Apr. 1998, 811-18.

Reilly, et al. "Endovascular repair of thoracoabdominal aneurysms: design options, device construct, patient selection and complications" J Cardiovasc Surg 2009; 50: 447-60.

Lam, et al. "Spinal cord protection with a cerebrospinal fluid drain in a patient undergoing thoracic endovascular aortic repair" J Vasc Interv Radiol. Sep. 2010;21(9):1343-6.

Zipfel, et al. "Spinal cord ischemia after thoracic stent-grafting: causes apart from intercostal artery coverage" Ann Thorac Surg. Jul. 2013;96(1):31-8.

Uchida, et al. "How to prevent spinal cord injury during endovascular repair of thoracic aortic disease" Gen Thorac Cardiovasc Surg. Jul. 2014;62(7):391-7.

Banga, et al. "Neuromonitoring, Cerebrospinal Fluid Drainage, and Selective Use of Iliofemoral Conduits to Minimize Risk of Spinal Cord Injury During Complex Endovascular Aortic Repair" J Endovasc Ther. Feb. 2016;23(1):139-49.

Fukui, et al. "Development of Collaterals to the Spinal Cord after Endovascular Stent Graft Repair of Thoracic Aneurysms" Eur J Vasc Endovasc Surg. (2016).

Akasaka, et al. "Evaluation of Spinal Cord Ischemia with a Retrievable Stent Graft Is Useful for Determining the Type of Repair for a Case of Patch Aneurysm" Ann Vasc Surg 2014; 28: 1313.e1-1311.e3.

Bosco, et al. "Set up of motor function monitoring for transoral approach to the upper cervical spine: a preliminary experience" Minerva Anestesiologica 2012, vol. 78, No. 7, 851-853.

Chun, et al. "A retrievable rescue stent graft and radiofrequency positioning for rapid control of noncompressible hemorrhage" J Trauma Acute Care Surg 2017, vol. 83, No. 2, 249-255.

Sattah, et al "Complications and Perioperative Management of Patients Undergoing Thoracic Endovascular Aortic Repair" J Intensive Care Med. Jul. 2018;33(7):394-406. doi: 10.1177/0885066617730571. Epub Sep. 25, 2017.

Kawaguchi, et al. "Prediction of spinal cord ischemia with a retrievable stent graft on endovascular treatment for a case of thoracic aortic aneurysm" Jpn J Thorac Cardiovasc Surg. Oct. 1998;46(10):1047-51.

Koizumi, et al. "Evaluation of spinal cord ischemia in endovascular stent graft repair and surgical operation of descending thoracic or thoracoabdominal aortic aneurysms" Kyobu Geka. Apr. 2004;57(4):262-7.

* cited by examiner

METHOD FOR TESTING INSURGENCE OF SPINAL ISCHEMIA DUE TO ENDOVASCULAR TREATMENT OF AORTIC ANEURISMS

This application is a continuation of and claims the benefit of U.S. patent application Ser. No. 14/116,021, filed on Nov. 6, 2013, which is a National Stage Entry of PCT/IB2012/052302, filed on May 9, 2012, which claims the benefit of Italian Priority No. MI2011A000796, filed on May 10, 2011. Each of these applications are hereby incorporated by reference in their entirety as if fully set forth herein.

The present invention relates to a removable implantable medical device in blood vessels, particularly for implantation in the thoracic aorta affected by aneurysm.

An aneurysm is a pathology that manifests itself as a variable and non-reversible dilation of a blood vessel.

Specifically, Thoracic Aortic Aneurysm (TAA) is a dilation of the thoracic aorta.

An aneurysm is a pathology that develops progressively in that at every dilation of the wall of the vessel there is a corresponding increase in the radial tension acting on the wall and thus a further action of expansion on the vessel.

This pathology is treated by administering pharmaceuticals or, in more serious cases, by surgery, the latter being particularly recommended for aneurysms larger than 6 centimeters.

Surgery to treat an aneurysm substantially consists of surgical prosthetic substitution with thoracotomic and laparotomic access of an aortic segment, with sequential clamping and reimplantation of collateral arteries.

An alternative method of surgical treatment to the conventional method uses endovascular techniques, which make it possible for the aneurysm to be covered by positioning a vascular endoprosthesis, which is substantially a synthetic duct that is adapted to functionally substitute the portion of vessel affected by aneurysm. In particular, by inserting and positioning the vascular prosthesis at the vessel affected by aneurysm, a "new lumen" for blood circulation is created which prevents the blood flow from exerting a pressure on the deformed walls that surround the aneurysm. The blood in the pockets defined between the outer walls of the vascular prosthesis and the deformed walls of the blood vessel is not subjected to any pressure force and rapidly coagulates.

Unfortunately, both conventional surgery and endovascular surgery are still associated with a significant mortality rate owing mainly to peri- and post-operative complications.

In surgery to repair a thoracic aortic aneurysm, there is the risk of causing spinal cord ischemia, owing to the reduction in the blood supply to the spinal cord due to sacrificing the intercostal arteries, which are essential for the perfusion of the spinal cord.

In particular, in the surgical treatment of large aneurysms of the thoracic aorta and in patients who have previously undergone thoracic or abdominal vascular surgery, there is a high risk of paraplegia, deriving from the possible onset of spinal cord ischemia.

The main limitation of this type of intervention is that the risk of causing spinal cord ischemia can be identified only during surgery and it manifests only following the surgery.

In the current state of the art, in order to monitor the functionality of the spinal cord during surgery or endovascular treatment of the thoracic aorta, neurophysiological parameters relating to the medullary function are read, and in particular the descending motor nerve pathways and ascending somatosensory nerve pathways are monitored.

With conventional surgery, when ischemic suffering is detected, an intraoperative therapy is immediately begun to improve the perfusion of the spinal cord, which essentially consists of increasing the availability of oxygen to the spinal cord, so as to increase the arterial pressure, the cardiac flow-rate, the concentration of hemoglobin, the saturation of oxygen and reduce the endoliquoral pressure. If this therapy is not sufficient to re-establish the medullary function, the surgeon will anastomize the intercostal vessels that were sacrificed during surgery so as to restore collateral circulation in order to get the blood to the spinal cord.

If the ischemic suffering is detected during implantation of the endovascular prosthesis, the only possible solution is to resort to medical therapy (increase spinal perfusion pressure, by increasing arterial pressure, cardiac flow rate and reducing liquoral pressure).

Thus, nowadays the main limitation of surgery by way of inserting an implantable medical device at the portion of vessel affected by aneurysm is the impossibility of predicting whether the positioning of this device inside the blood vessel can cause the arrest of the blood flow in the surrounding vessels.

Thus, in the treatment of aneurysms, particularly of aneurysms of the thoracic aorta, by endovascular prostheses, the need is particularly felt to assess the risks of onset of ischemic suffering before the definitive implantation of the endovascular prosthesis. More specifically, for thoracic aortic aneurysms, it is necessary to test whether the grafting of the endovascular prosthesis can cause the arrest of the blood flow in the vessels that supply the spinal cord.

The techniques currently developed to achieve this aim use endovascular devices that cause the blocking of the intercostal arteries and of the aorta so as to evaluate the response of the organism by monitoring the evoked potentials of the spinal cord.

For example, blocking the aortic portion in which the aneurysm is present is simulated by inserting two balloons at the two ends of the aneurysm itself. In this case it is mandatory to use a machine for extracorporeal circulation in order to ensure the perfusion of the parts downstream of the blocked aorta.

US2005/0131515, US2009/0171441 and WO2008/016578 describe prostheses of the definitive type, i.e. prostheses that are not capable of blocking the collateral vessels of the aorta only temporarily, so as to be able to be used in an emergency in acute aortic syndromes, awaiting a definitive prosthesis.

In substance, the prostheses in the cited prior art documents, while being removable, are not capable of provisionally simulating the operation of a definitive prosthesis, in that they are designed as prostheses for therapeutic use and not for preventive and diagnostic use. Moreover it is not possible for such devices to be removable if they are the cause of a medullary ischemia previously detected in the operating theater with adapted monitoring methods.

US2005/0131515 differs furthermore in the absence of a lumen for guiding, the impossibility of varying the prosthetic caliber inside the vessel, the necessity for prework before the implantation (see heating of the prosthesis), and the impossibility of positioning following removal.

US2009/0171441 differs in that it is constituted by a plurality of separate units and in the impossibility of varying the prosthetic caliber inside the vessel.

WO 2008/016578 differs in that it can be repositioned only during the procedure. Once released in the position and with the diameter adjusted it is not removable.

The aim of the present invention is to provide a device for verifying the arrest of the blood flow in blood vessels during the endovascular treatment of aneurysms.

Within this aim, an object of the invention is to provide a device that does not cause blocking of the vessel.

Another object of the invention is to provide a device that does not necessitate means for extracorporeal circulation of the blood.

Moreover, an object of the present invention is to provide a device that is highly biocompatible.

In more detail, the present invention sets out to provide an implantable device that can be easily inserted in the vessel and which can be precisely arranged at the portion affected by aneurysm.

Moreover, the present invention sets out to provide an implantable medical device that is compatible with the techniques and instruments normally and usually used for the endovascular treatment of aneurysm.

Another object of the invention is to provide a device that is highly reliable, easy to implement and low cost.

This aim and these and other objects which will become better apparent hereinafter are achieved by an implantable and removable medical device for the endovascular treatment of aneurysm, particularly of aneurysm of the thoracic aorta, comprising a supporting structure which has a substantially tubular shape and is covered externally by a covering, to define a duct for blood circulation, characterized in that it comprises extraction means for extracting said duct from the body of the subject in whom it is inserted, said extraction means being associated with said duct and communicating with the outside of said body.

Further characteristics and advantages of the invention will become better apparent from the description of a preferred, but not exclusive, embodiment of the implantable medical device according to the invention, which is illustrated by way of non-limiting example in the accompanying drawings wherein.

Figure 1:
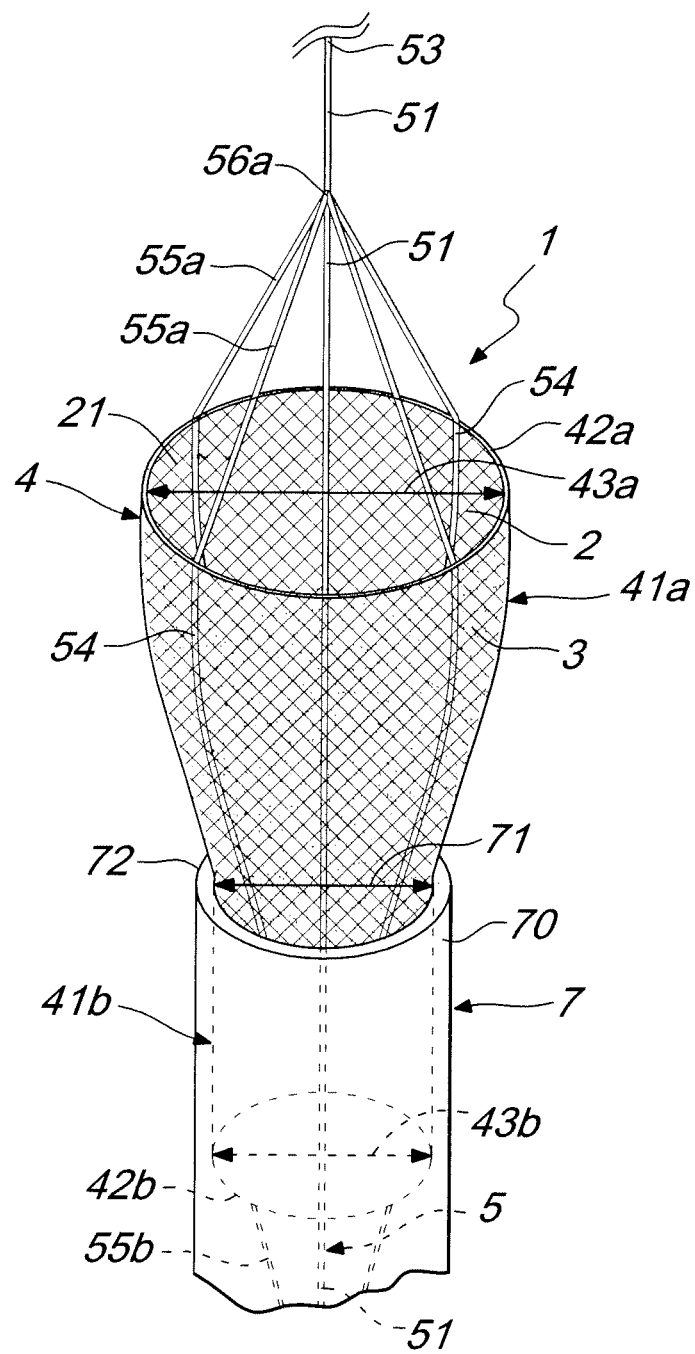
FIG. 1 is a perspective view of an implantable medical device according to the invention.

With reference to the figures, the implantable device according to the invention, generally designated with the reference numeral 1, which can be used during the procedure for the endovascular treatment of aneurysm, particularly of aneurysm of the thoracic aorta, comprises a supporting structure 2 which has a substantially tubular shape and is covered externally by a covering 3.

The supporting structure 2 and its covering 3 define a duct 4 for blood circulation, and in particular this duct substitutes the deformed portion of vessel so as to create a "new lumen" that allows blood circulation within it and does not arrest the blood flow.

The peculiarity of the device 1 according to the invention consists in that it comprises extraction means 5 for extracting the device from the body of the subject undergoing the surgery. The extraction occurs by sliding the device 1 through the blood vessels until it is completely outside 6 the body.

The extraction means 5 are associated with the duct 4 of the device 1 and they communicate with the outside 6 of the body.

Advantageously the extraction means 5 are a cable 51 within which it is possible to slide an angiographic guide wire 53, which exits from the end 56 made of biocompatible material connected with the duct 4.

In a particularly advantageous embodiment, the cable 51 passes through the duct 4 internally along its principal direction of extension, exiting by a few centimeters, thus allowing the free travel of the angiographic guide wire 53. Between the perimeters 42a and 42b of the bases of the duct 4 there are wires 54 which extend along the entire body of the duct 4.

At each perimeter 42a and 42b, the wires 54 continue in two cords, respectively 55a and 55b, which are directed toward the inside of the radial cross-section of the duct 4 and which join at a point of attachment, respectively 56a and 56b, with the cable 51.

The cords 55 make it possible to associate the duct 4 with the cable 51, which in operational terms constitutes the means of extraction of the duct 4 from the body, i.e. it is the means that functionally makes it possible to obtain the sliding of the duct 4 inside the blood vessels.

Figure 2:
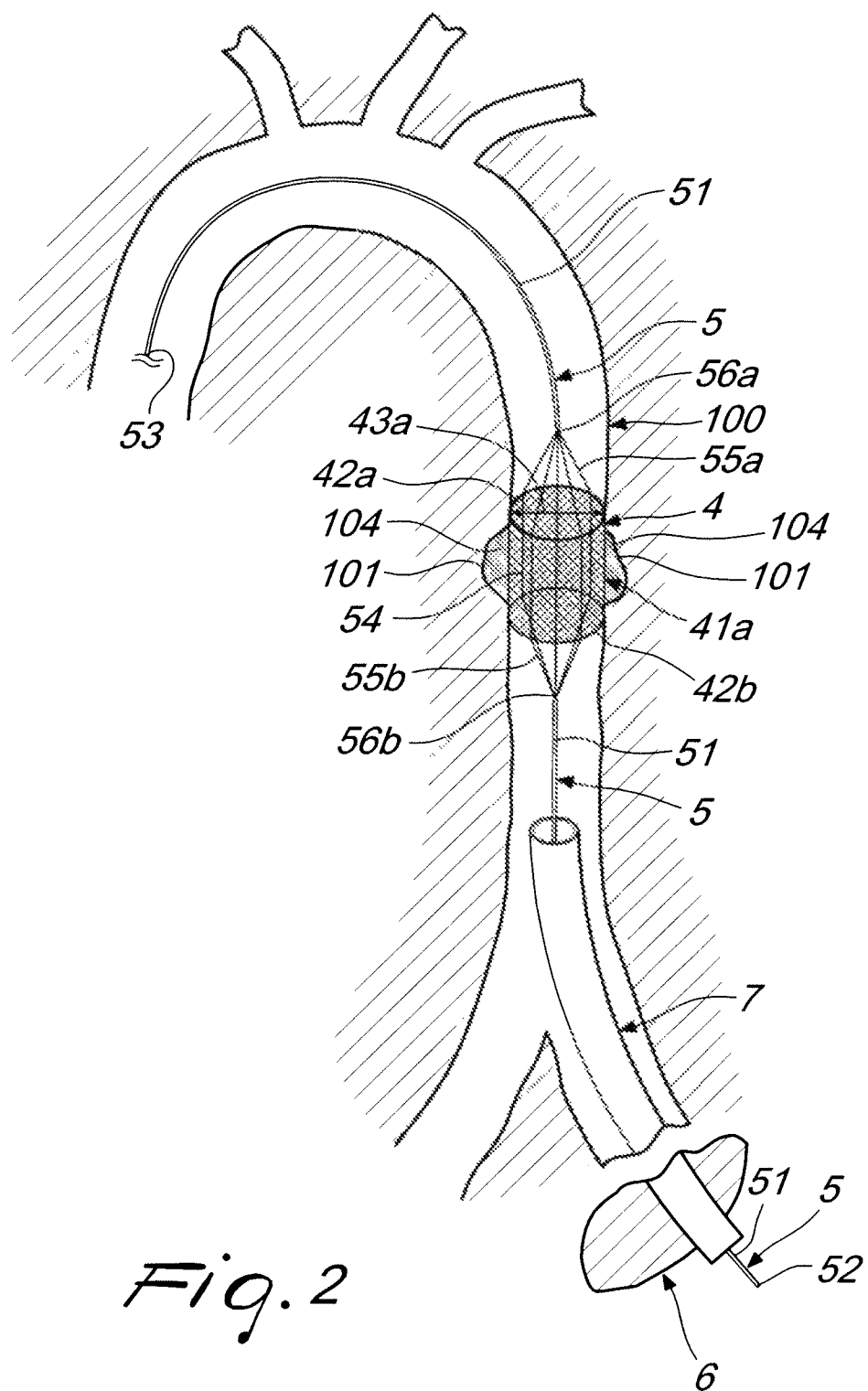
FIG. 2 is a schematic diagram of the implantable medical device, according to the invention, positioned in the blood vessel with the aneurysm.
Figure 3:
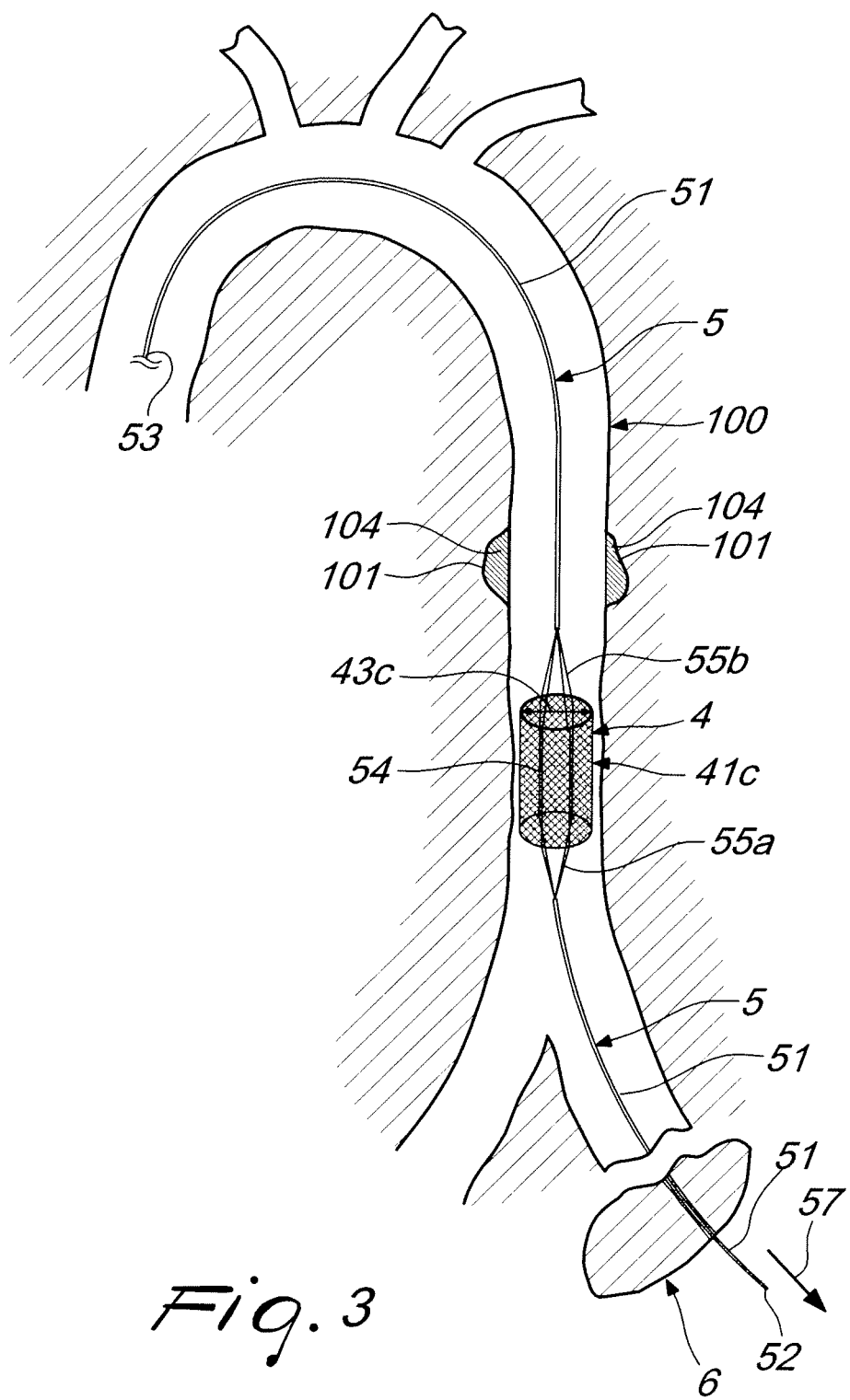
FIG. 3 is a schematic diagram of the medical device according to the invention in the extraction configuration.

With reference to FIG. 2, the duct 4 is positioned inside the blood vessel 100 at the walls 101 deformed by the aneurysm. In particular, the length of the duct 4 along its principal direction of extension is greater than the length of the portion of vessel 100 deformed by the aneurysm.

In this manner the device 1 defines a passage channel for the blood which is defined inside the vessel 100 itself and especially it completely prevents the blood from entering the pockets 104 that form between the deformed walls 101 of the vessel 100 and the outer wall of the duct 4. The blood that stays locked in the pockets 104 following the grafting of the duct 4 rapidly coagulates.

Advantageously the supporting structure 2 is a meshed fabric, for example it is a net of wires 21 that are interleaved in a zigzag pattern.

The wires 21 which constitute the supporting structure 2 are made of biocompatible metallic material, preferably stainless steel or alloys of nickel and titanium, better known as "nitinol".

"Nitinol" alloys are particularly adapted for this application because they are shape-memory materials, for their ability to adapt to considerable tensions and because they have a high level of physiological and chemical compatibility with the human body.

Advantageously the covering 3 is made of biocompatible polymeric material, such as for example Dacron® or PTFE, or it can be a biological material, of animal or human origin, pharmacologically and chemically treated.

Preferably the covering 3 is sewn onto the zigzag wires 21 that constitute the supporting structure 2.

The medical device 1 assumes a compressed configuration 41b and an active configuration 41a, which is the configuration that the duct 4 assumes when it is positioned at the aneurysm.

In the compressed configuration 41b the duct 4 has a first radial dimension 43b which is smaller than a second radial dimension 43a of the duct 4 in the active configuration 41a.

In greater detail, the compressed configuration 41b is obtained by way of compression of the duct 4 inside a sheath 70 of a catheter 7 that has a diameter 71 which is smaller than that of the duct 4 in its active configuration 41a.

The compression of the duct 4 inside the catheter 7 is obtainable thanks to the elasticity of the material defining the supporting structure 2.

The compressed configuration 41b obtained when the device 1 is inserted in the catheter 7 is necessary during the step of insertion of the device 1 in the blood vessel 100.

In particular, initially the catheter 7 is inserted in the body and is made to pass through blood vessels until it arrives proximate to the portion of vessel 100 that is deformed by aneurysm. Subsequently the device 1 is inserted in the catheter 7 and assumes its compressed configuration 41b. The operator, acting on the cable 51, makes the device 1 advance inside the catheter 7 until it reaches the end tip 72 of the catheter 7 by making it slide in safety in the guide which was previously positioned in the aorta and which functions as a "rail". The device 1, exiting from the containment sheath 70 defined by the catheter 7, is positioned at the aneurysm, and expands to assume an active configuration 41a, which is characterized in that it has a second radial dimension 43a which is greater than the first radial dimension 43b assumed by the duct 4 in the compressed configuration 41b.

The extraction means 5 activate an extraction configuration 41c in which the duct 4 assumes a third radial dimension 43c which is smaller than the first radial dimension 43b assumed in the active configuration 41a.

Advantageously the third radial dimension 43c is smaller than the diameter of the blood vessel in which it is implanted and also of the vessels that it must pass through in order to arrive outside 6 the body of the subject.

Preferably the third radial dimension 43c is substantially equal to that 41a assumed in the compressed configuration 41b so as to enable the device to be reinserted in the catheter 7 at the end tip 72 and slide inside the latter until it arrives outside 6 the body.

Thanks to this radial contraction, the implantable medical device 1 can be extracted outside 6 body without damaging the interior of the blood vessel or vessels during the passage through them.

In greater detail, by pulling the end 52 of the cable 51 outside 6 the body in the direction of extraction 57, first the cords 55b, then the wires 54 and finally the cords 55a are all subjected to traction. By way of this traction, the duct is elongated along its principal direction of extension and is contracted radially, until it assumes the extraction configuration 41c.

The means 5 of extracting the device 1 are activated after the detection, by way of detection electrodes (not shown in the accompanying figures) of evoked potentials generated in response to a stimulation achieved by way of stimulation electrodes.

An example of use of the device 1 according to the invention shall now be described below.

First the catheter 7 is inserted through the femoral artery, from where it is made to ascend to the aorta and halt proximate to the portion of vessel 100 deformed by aneurysm.

Subsequently the device 1 is inserted in the catheter 7, which, assuming its compressed configuration 41b, is pushed into the catheter 7 until it reaches the end tip 72 thereof. The end 52 of the cable 51 that constitutes the extraction means 5 remains outside 6 the body of the subject in whom the device 1 is inserted. Specifically, it exits at the point where the incision necessary for the insertion of the catheter 7 was made.

The device 1, exiting from the end tip 72 of the catheter 7, expands at the portion affected by aneurysm. Thus the device 1, assuming its active configuration 41a, substitutes the walls of the vessel 100 affected by aneurysm by defining a duct 4 for blood circulation and blocking the entry of blood into the pockets 104.

Once the device is positioned at the portion of vessel 100 affected by aneurysm, neurophysiological monitoring can be carried out of the functions of the spinal cord in order to evaluate whether the insertion of the device 1 has caused the blocking of blood vessels that supply the spinal cord.

Such monitoring can be performed by way of an adapted apparatus, generally constituted by stimulators and amplifiers connected to a processor and a screen for displaying traces of somatosensory and motor potentials.

Somatosensory potentials are electrical signals detected on the scalp of the patient at the somatosensory cortex. They derive from the repetitive stimulation at a certain frequency and power of a peripheral nerve, such as the rear tibial nerve. The stimulation applied in the region of the ankle is recorded at the popliteus and then at the lumbar and cervical regions and finally in the cortex.

The motor potentials are obtained following high-intensity external stimuli applied to the scalp at the motor cortex and by recording the muscular contraction in the peripheral region, in the feet and legs. The high-intensity stimulation has the drawback of causing small muscular jolts, which could make the procedure less easy. Moreover, sometimes the introduction into the femoral artery can be responsible for ischemia in the corresponding lower limb thus rendering the monitoring of the motor and somatosensory pathway unusable on that side.

For these reasons, an alternative is the low-energy stimulation of the motor cortex and detection of the response of the corticospinal motor pathways in the spinal cord, under the presumed bodily location of injury, by way of an electrocatheter inserted previously in the epidural space. The evoked potential that is generated in the spinal cord (D wave), corresponding to the activation of the descending corticospinal fascicle, also has the advantage of not being depressed in the presence of muscle relaxants, and moreover it provides important prognostic information (the absence of the muscle motor potential but the persistence of the D wave are indicative of a good outcome in the long term while only the concomitant absence of the D wave and of the motor potential are indicative of negative outcomes with paraplegia). Moreover the epidural electrocatheter would make it possible to explore the somatosensory pathway by epidural electrical stimulation if it is not possible to stimulate the rear tibial nerve owing to ischemia of the lower limb.

Any signs of suffering of the spinal cord, and hence of symptoms of a possible risk of onset of spinal cord ischemia, are manifested as significant reductions in the values of the recorded somatosensory and motor potentials. In particular these reductions are over 40 or 50% with respect to the basal values.

After the monitoring of evoked potentials, the means of extracting the device are activated, which make the device 1 assume the extraction configuration 41c in order to allow the removal by sliding within the vessels without damaging their intima. In greater detail, the cable 51 is held by the operator at the end 52 outside 6 the body of the subject in whom the device 1 is implanted, and it is gently pulled in the direction of extraction 57 so as to make it slide inside the vessels until the duct 4 is completely outside 6 the body of the subject in whom it had been implanted.

By assessing the values of the evoked somatosensory and motor potentials, the specialist can evaluate whether the implanting of the device 1 has caused the onset of ischemic suffering as a consequence of its presence at the portion of vessel 100 affected by aneurysm.

Thanks to this evaluation the specialist decides whether to treat the aneurysm by way of inserting a definitive endovascular prosthesis (and to evaluate the extension thereof) or whether to opt for other methods of intervention.

In practice it has been found that the device according to the invention fully achieves the intended aim in that it makes it possible to verify the arrest of the blood flow in blood vessels in the endovascular treatment of aneurysm.

The fact that the device comprises a tubular-shaped support covered by a covering makes it possible to define a duct that allows blood to circulate within it without causing the blocking of the vessel and without necessitating means for extracorporeal circulation.

The fact that the supporting structure is made of biocompatible metallic material, the fact that the covering is made of biocompatible polymeric or biological material and moreover the fact that the cable for extraction is made of biocompatible material, makes it possible to obtain a device that is highly biocompatible overall.

Moreover the fact that the device can assume a compressed configuration enables its insertion and sliding inside a catheter, in this manner facilitating the operation of positioning at the aneurysm.

The fact that the device can assume an extraction configuration in which the radial dimension is smaller than that assumed in the active configuration makes it possible to make the device slide inside vessels without damaging their intima.

Finally the device according to the invention can be used in combination and is compatible with the techniques and instruments normally and usually used for endovascular treatment, such as for example angiographic guide wires and valved catheter introducers.

Moreover, the architectural material used, i.e. nitinol, an alloy of nickel and titanium which in opening outside the jacket tends to reach the nominal diameter without appreciable elongation or shortening of the structure in different calibers (this makes it possible to have the exact length in every measurement of the aortic segment to be excluded, and subsequently to have the right length of the definitive prosthesis).

The presence of the guide inside the device enables a less traumatic endovascular management of the entire system, in any cranial or caudal movements thereof, and the possibility of shortening passages for the various measurements.

Nitinol moreover enables the construction of small caliber systems, with possible percutaneous approach.

Such possibility thus also enables the optional monitoring of the patient with functional RM, both in the perioperative period and in preoperative planning if any (locating the great radicular artery in RM with the device positioned). The great radicular artery of Adamkiewicz is the arterial vessel that most greatly affects the perfusion of the spinal cord and it has a variable origin in the abdominal thoracic aorta.

Although the device according to the invention has been conceived in particular for positioning at aneurysms of the thoracic aorta, it can also be used, more generally, for aneurysms present in other blood vessels or in urgent use in rupturing aortic aneurysms (temporary urgent blocking of the aneurysm without arresting flow, as an alternative to clamping in urgent laparotomy or to percutaneous positioning of occluding balloon, while awaiting an open or endovascular surgical solution).

The device, thus conceived, is susceptible of numerous modifications and variations, all of which are within the scope of the appended claims. Moreover, all the details may be substituted by other, technically equivalent elements.

In practice the materials employed, as well as the contingent dimensions and shapes, may be any according to requirements and to the state of the art.

The content of Italian patent application no. MI2011A000796, the priority of which is claimed in the present application, is incorporated as a reference.

The invention claimed is:

1. A method for testing insurgence of spinal ischemia due to endovascular treatment of aortic aneurisms, the method comprising:
providing an implantable and removable medical device for endovascular insertion in the thoracic aorta, said medical device comprising a supporting structure which has a substantially tubular shape and is covered externally by a covering, to define a duct for blood circulation, said device comprising extraction means for extracting said duct from a body of a patient in whom it is inserted, said extraction means being associated with said duct and communicating with an outside of said body;
introducing said device in a segment of the thoracic aorta where an aneurism is formed;
defining a duct for blood circulation with the device;
expanding the duct to make a wall of the segment radially impervious to blood, thereby reducing blood flow through the patient's intercostal arteries;
applying a stimulus to the patient's motor cortex;
recording muscular contractions in a patient's peripheral region in response to the stimulus;
evaluating a patient response to reduction of blood flow through the intercostal arteries based on the recorded muscular contractions; and
selecting an aneurism treatment method based at least in part on the evaluation.

2. The method of claim 1, wherein the extraction means comprises a biocompatible cable, a first end of the cable being attached to the device and a second end of the cable protruding from the patient.

3. The method of claim 1, wherein a length of the duct defined by the device is greater than a length of the segment deformed by the aneurism in order to avoid an inflow of blood into pockets defined between the deformed portion of blood vessel and an outer surface of the duct.

4. The method of claim 1, wherein the supporting structure comprises a meshed fabric made of biocompatible metallic material.

5. The removable implantable medical device according to claim 4, wherein the biocompatible metallic material comprises an alloy of nickel and titanium.

6. The method of claim 1, wherein the covering comprises a biocompatible polymeric material.

7. The method of claim 1, wherein the covering is sewn onto the supporting structure.

8. The method of claim 1, wherein the device assumes an active configuration, defined by a first radial dimension of the duct for defining a passage lumen for blood flow, and a compressed configuration, defined by a second radial dimension of the duct for moving the device inside a catheter for insertion, the second radial dimension being smaller than the first radial dimension.

9. The method of claim 8, wherein the extraction means activate an extraction configuration defined by a third radial dimension of the duct for avoiding damage to the intima of blood vessels during extraction, the third radial dimension being smaller than the first radial dimension.

10. The method of claim 9, wherein the third radial dimension is substantially equal to said second radial dimension.

11. The method of claim 1, further comprising:
  selectively activating the extraction means in response to the recorded muscular contractions.

\* \* \* \* \*